US00PP09614P

United States Patent [19]

Van Der Voort

[11] Patent Number: Plant 9,614

[45] Date of Patent: Jul. 30, 1996

[54] PLANT NAMED "WOODRIFF'S MEMORY"

[75] Inventor: Cees A. Van Der Voort, Katwijk, Netherlands

[73] Assignee: Vletter & Den Haan Beheer B.V., AE Rijnsburg, Netherlands

[21] Appl. No.: 440,662

[22] Filed: May 15, 1995

[51] Int. Cl.[6] ..... A01H 5/00

[52] U.S. Cl. ..... Plt./87.4

[58] Field of Search ..... Plt./87.4

*Primary Examiner*—James R. Feyrer

*Attorney, Agent, or Firm*—Foley & Lardner

[57] ABSTRACT

A lily plant named Woodriff's Memory particularly characterized by its large open light-pink flowers measuring approximately 21 cm in diameter and tepals with spots on lower half.

1 Drawing Sheet

The present invention comprises a new and distinct cultivar of lily, botanically known as Lilium Oriental Hybrid and hereinafter referred to by the cultivar name Woodriff's Memory.

The new cultivar is a product of a planned breeding program which had the objectives of creating new lily cultivars with an intense pink color and large upright flowers.

Woodriff's Memory was originated from a hybridization made by the inventor in a controlled breeding program in Rijnsburg, The Netherlands in 1983. The male and female parents were unnamed and proprietary seedlings.

Woodriff's Memory was discovered and selected as one flowering plant within the progeny of the stated cross by the inventors in July 1986 in a controlled environment in Rijnsburg, The Netherlands.

The first act of asexual reproduction of the new cultivar was accomplished by the inventors when scales were taken in 1987 from the initial selection in a controlled environment in Rijnsburg, The Netherlands. Horticultural examination of selected units has demonstrated that the combination of characteristics as herein disclosed for Woodriff's Memory are firmly fixed and are retained through successive generations of asexual reproduction.

The new cultivar has not been observed under all possible environmental conditions. The phenotype may vary significantly with variations in environment such as temperature, light intensity, and day length, without, however, any variance in genotype. The following observations, measurements and comparisons describe plants grown in Wageningen, The Netherlands under greenhouse conditions which approximate those generally used in commercial practice.

The following traits have been repeatedly observed and are determined to be basic characteristics of Woodriff's Memory which, in combination, distiguish this lily as a new and distinct cultivar.

1. Large open light-pink flowers with the upper surface of the tepals having a color value of RHS 73C.
2. Tepals have spots on lower half.
3. The flower measures approximately 21 cm in total diameter.

Of the many commercial cultivars known to the present inventory, the most similar in comparison to Woodriff's Memory is Belcanto, as disclosed in U.S. Plant Pat. No. 8,309. In comparison to Belcanto, the new cultivar has smaller flowers and a more intense flower color.

The accompanying photographic drawngs show typical flower characteristics of Woodriff's Memory, with colors being as true as possible with illustrations of this type. In the following description, color references are made to The Royal Horticultural Society [R.H.S] Colour Chart. The color values were determined at Wageningen, The Netherlands in June 1994.

Origin: Seedling from breeding program.

Parentage:

*Seed parent.*—Unnamed seedling.

*Pollen parent.*—Unnamed seedling.

Classification:

*Botanical.*—Lilium cv. Woodriff's Memory.

*Commercial.*—Oriental hybrid.

Plant:

*Form.*—A single stem carrying numerous pedicels alternately arranged.

*Height.*—On opening of anthers of first flower medium.

*Growth habit.*—Vigorous.

*Stem.*—Circular in transverse section; internodal length uniform.

*Foliage.*—Quantity: From small to medium leaves depending on growing conditions. Size of leaf: Mature leaves are approximately 2.6 cm wide and 13 cm long. Shape of leaves: Generally ovate. Color: RHS 137B.

*Bulbs.*—Size: 16–18 cm circumference. Color: White.

Bud:

*Form.*—Tapering like a lancet.

*Size.*—cm in length depending on growing conditions.

*Opening.*—Unfolds normally.

*Color.*—RHS 145D.

*Tepals.*—Folded, three visible.

Flower:

*Blooming habit.*—Raceme.

*Size.*—21 cm in total diameter depending on growing conditions.

*Borne.*—Upright.

*Shape.*—Generally hexagonal star in form and bowl-shaped n cross-section.

*Tepalage.*—Number of tepals: Six. Arrangement: Three inner and three outer. Color (upper surface): Light-pink (RHS 73C); variegated. Color (lower surface): Light-pink (RHS 73D). Spotting or marking: Spots (RHS 61C) are present on lower half of tepal. The color of the midvein near the base of the tepals is RHS 2D.

*Pedicel.*—Length: 10 cm (first flower) depending on growing conditions. Color: Medium green with anthocyanin pigmentation. Form: Slightly curved.

*Texture.*—Papillose

*Disease resistance.*—disease problems noted to date.

*Fragrance.*—Present.
*Lasting quality.*—Excellent.
Reproductive organs:
*Stamens and anthers.*—Arrangements: Anthers form a generally circular pattern at their upper ends. Length: 8 cm. Number: Six. Filaments: Yellow (RHS 30).
*Pollen color.*—Light-Brown. (RHS 34B)
*Anther color.*—RHS 172D.

*Pistils.*—Green. (RHS 145D).
*Stigma.*—Purple. (RHS 145D)
*Ovaries.*—Triangular in shape.

It is claimed:

1. A new a distinct lily plant named Woodriff's Memory as described and illustrated.

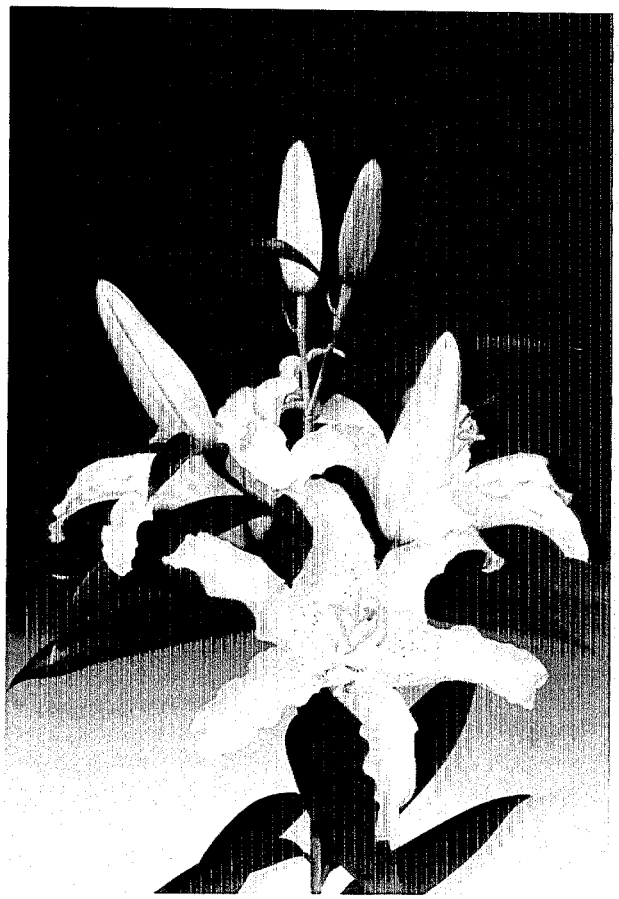

* * * * *